(12) United States Patent
Huang

(10) Patent No.: US 11,399,710 B2
(45) Date of Patent: Aug. 2, 2022

(54) LARYNGOSCOPE BLADE AND LARYNGOSCOPE

(71) Applicant: Zhuhai Pusen Medical Technology Co., Ltd., Guangdong (CN)

(72) Inventor: Honghui Huang, Guangdong (CN)

(73) Assignee: Zhuhai Pusen Medical Technology Co., Ltd., Zhuhai (CN)

( * ) Notice: Subject to any disclaimer, the term of this patent is extended or adjusted under 35 U.S.C. 154(b) by 201 days.

(21) Appl. No.: 16/583,783

(22) Filed: Sep. 26, 2019

(65) Prior Publication Data

US 2020/0337546 A1 Oct. 29, 2020

(51) Int. Cl.
*A61B 1/267* (2006.01)
*A61B 1/00* (2006.01)

(52) U.S. Cl.
CPC .......... *A61B 1/267* (2013.01); *A61B 1/00098* (2013.01)

(58) Field of Classification Search
CPC ...................................................... A61B 1/267
USPC ................................................ 600/184–245
See application file for complete search history.

(56) References Cited

U.S. PATENT DOCUMENTS

| 2009/0270686 | A1* | 10/2009 | Duke ..................... A61B 1/127 600/203 |
| 2011/0077466 | A1* | 3/2011 | Rosenthal .............. A61B 1/042 600/188 |
| 2012/0095295 | A1* | 4/2012 | McGrath ........... A61M 16/0488 600/194 |
| 2013/0237763 | A1* | 9/2013 | Qiu ........................ A61B 1/267 600/188 |
| 2014/0343581 | A1* | 11/2014 | Lee ......................... A61B 17/10 606/151 |
| 2018/0132709 | A1* | 5/2018 | Chen .................. A61B 1/00045 |

* cited by examiner

*Primary Examiner* — Eduardo C Robert
*Assistant Examiner* — Tara Rose E Carter

(57) ABSTRACT

Disclosed is a laryngoscope blade and a laryngoscope. In order to solve the problem that the small-sized catheter is not in place, the present disclosure is provided with an elastic mechanism at the distal end of the guide groove of the laryngoscope blade, and the elastic mechanism can be elastically deformed. On one aspect, the top of small-sized catheter can be pressed against the spatula, and on the other aspect, the elastic mechanism is pushed away from the spatula by the large-sized one, so that the laryngoscope blade and the laryngoscope equipped with the laryngoscope blade can be adapted to fit different sizes of catheters, and the scope of application is wider With better effect.

11 Claims, 6 Drawing Sheets

LARYNGOSCOPE BLADE AND LARYNGOSCOPE

CROSS REFERENCE TO RELATED APPLICATIONS

The present application claims the benefit of Chinese Patent Application No. 201910336414.4 filed on Apr. 25, 2019, the contents of which are incorporated herein by reference in their entirety.

TECHNICAL FIELD

The present disclosure relates to medical devices, and more particularly to a laryngoscope blade and a laryngoscope.

BACKGROUND

Laryngoscopes are the most commonly used for cannula tools and are generally constructed of spatulas, handles, and light sources. The aim of the laryngoscope is to lift the mandibular and anterior oropharyngeal soft tissue up to make the glottis exposed, and a tracheal catheter is passed through the glottis into the trachea under direct vision. The visual laryngoscope is equipped with a camera on the spatula of the traditional laryngoscope. It can observe the unobstructed sight of the naked eye and solve the problem of poor exposure of the difficult airway glottis in the traditional laryngoscope. However, it brings another problem that the angle between the glottis and the mouth seen on the video is too large, the tracheal catheter is difficult to reach the glottis, and additional tools are needed to assist in delivering the tracheal catheter to the glottis, which is cumbersome and has a high failure rate.

In response to this situation, the new laryngoscope adds a guide groove to the spatula. The guide groove can guide the tracheal catheter to the glottis, but the guide groove is only fit for a suitable size of the tracheal catheter. When the tracheal catheter the size pass through the guide groove, it is easily displaced, the angle at which the tracheal catheter protrudes is greatly deviated from the axis of the camera, and it is difficult to be smoothly guided into place, the patient has a poor feeling after the tracheal catheter is displaced, which affects the treatment effect.

SUMMARY

In order to overcome the above deficiencies of the prior art, the present disclosure provides a laryngoscope blade and a laryngoscope which are compatible with different types of size of a tracheal catheter and ensure the accuracy of the position of the cannula.

In order to achieve the above object, the technical solution adopted by the present disclosure is:

A laryngoscope blade includes a spatula, at least one image channel disposed under the spatula; and a guide groove besides the image channel for allowing a catheter passing through; the guide groove includes at least one bottom plate extending in the same direction as the spatula, a distal end of the bottom plate is provided with an elastic mechanism pushing the catheter to the spatula.

As a further improvement of the above aspect, the elastic mechanism includes a guide plate arranged at the distal end of the bottom plate, a peak with the smallest distance between the guide plate and the spatula is provided on said guide plate facing one side of the spatula, which lifts the catheter.

As a further improvement of the above aspect, a front end of the guide plate is connected to the bottom plate, and the distal end of the guide plate is tilted toward the direction of the spatula.

As a further improvement of the above aspect, one side of the left and right sides of the guide plate is connected to the image channel, and the other side is tilted toward the spatula.

As a further improvement of the above aspect, the guide plate is provided with a projection.

As a further improvement of the above aspect, the guide plate is made of an elastic material.

As a further improvement of the above aspect, the junction of the bottom plate and the guide plate is provided with an elastic arm being made of an elastic material.

As a further improvement of the above aspect, the guide plate is hinged to the bottom plate, the guide plate is further connected with a reset device, and the reset device makes the guide plate having a tendency to rotate toward the spatula around a hinge shaft.

As a further improvement of the above aspect, the reset device is a first elastic member sleeved on the hinge shaft of the guide plate and the bottom plate, the first elastic member has an elastic force of circumferential torsion, and torsion bars on both sides of the first elastic member are respectively located below the bottom plate and the guide plate.

As a further improvement of the above aspect, the reset device is a second elastic member having an axial elastic force, and two ends of the second elastic member are respectively connected to the guide plate and the guide groove.

As a further improvement of the above aspect, the reset device is an elastic plate, and a lower end of the elastic plate is fixedly connected with the guide groove, and an upper end is in contact with one side of the guide plate facing away from the spatula, the elastic plate is made of an elastic material.

As a further improvement of the above aspect, the elastic mechanism includes a third elastic member disposed at the end of the bottom plate, and the third elastic member is located at the side of the guide plate facing the spatula, the third elastic member lifts the catheter.

As a further improvement of the above aspect, the elastic mechanism includes a projection block provided on the upper surface of the distal end of the bottom plate, said projection block is made of an elastic material.

A laryngoscope includes a handle coupled to any of the laryngoscope blade described above.

The beneficial effects herein are:

The present disclosure relates to a laryngoscope blade and a laryngoscope thereof, the laryngoscope blade includes spatula; at least one image channel disposed under the spatula; and a guide groove besides the image channel for allowing a catheter passing through; the guide groove includes at least one bottom plate extending in the same direction as the spatula, a distal end of the bottom plate is provided with an elastic mechanism pushing the catheter to the spatula; the laryngoscope includes a handle coupled to any of said laryngoscope blade. The elastic mechanism can press the catheter against the spatula, so that the catheter protrudes along the surface of the spatula, and the axial direction of the catheter is close to the axial direction of the image channel, which can accurately locate the position of the catheter and improve the accuracy of the catheter, thereby to improve the effectiveness of the examination treatment.

BRIEF DESCRIPTION OF THE DRAWINGS

In order to more clearly illustrate the technical solutions in the embodiments of the present disclosure, the accompanying drawings used in the description of the embodiments will be briefly described below. It is apparent that the described drawings are only a part of the embodiments of the present disclosure, and not all of the embodiments, and other designs and drawings can be obtained according to the drawings without any creative work by those skilled in the art.

DETAILED DESCRIPTION OF EMBODIMENTS

Figure 1:
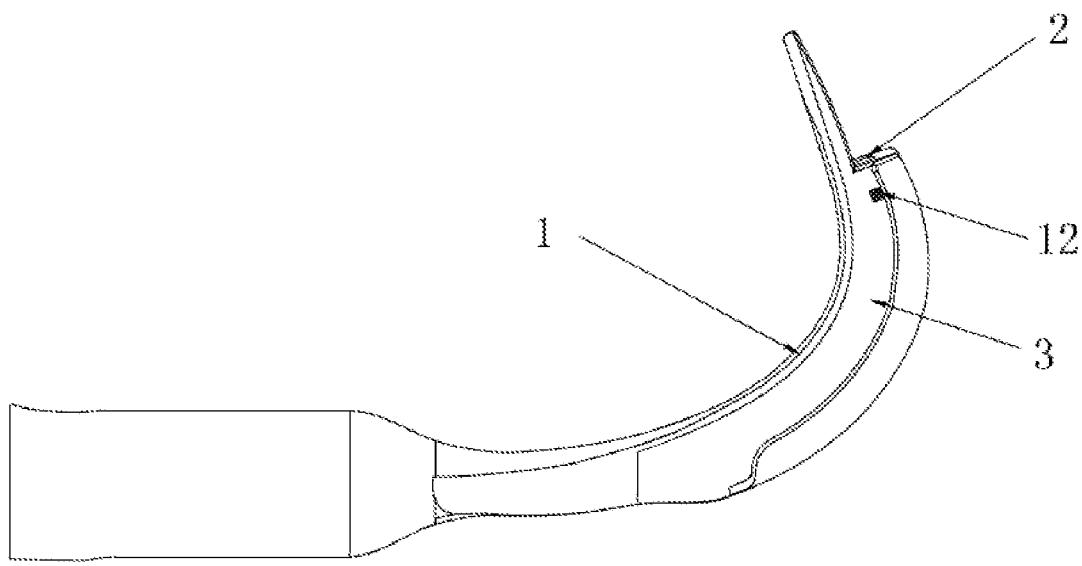
FIG. 1 is a left side view of the first embodiment of the present disclosure.

The concept, the specific structure and the technical effects of the present disclosure will be clearly and completely described in conjunction with the embodiments and the accompanying drawings. It is apparent that the described embodiments are only a part of the embodiments of the present disclosure, and not all of the embodiments, based on the embodiments of the present disclosure, other embodiments obtained by those skilled in the art without creative efforts belong to the scope of the present disclosure.

In the description of the present disclosure, it is to be noted that the terms "center", "upper", "lower", "left", "right", "vertical", "horizontal", "inside", "outside", "front", "rear" used as indications of orientation or positional relationship are based on the orientation or positional relationship shown in the drawings, and is merely for the convenience of the description of the present disclosure and the simplified description, and does not indicate or imply that the device or component referred to has a specific orientation, construction and operation in a particular orientation. It is thus not to be construed as limiting the invention. Moreover, the terms "first", "second" and "third" are used for descriptive purposes only and are not to be construed as indicating or implying relative importance.

It should be noted, unless otherwise explicitly stated and defined, that the terms "installation", "connected", and "connected" shall be understood broadly, and may be, for example, a fixed connection, a detachable connection, or an integral connection, a mechanical connection or an electrical connection; it can be directly connected or indirectly connected through an intermediate medium, which can be the internal connection of the two elements. The specific meaning of the above terms in the present disclosure can be understood in a specific situation by those skilled in the art.

Referring to FIGS. 1-11, a laryngoscope blade includes a spatula 1, at least one image channel 2 disposed under the spatula 1, and a guide channel 3 besides the image channel (2) for allowing a catheter passing through, the image channel 2 is used for loading an imaging device or a guiding device. Different image transmission devices, such as an electronic imaging device or an optical imaging device, or other various working devices may be disposed in the image channel 2, and the specific structure is not limited. The guide groove 3 includes a bottom plate 4 extending in the same direction as the spatula 1, the distal end of the bottom plate 4 is provided with an elastic mechanism. The elastic mechanism pushes the catheter toward the spatula 1 such that the axis of the catheter is almost parallel to that of the image channel. When the smaller-sized catheter passes through the guide groove 3, the elastic mechanism can press the catheter against the spatula 1, so that the catheter protrudes along the surface of the spatula 1. The axial direction of the catheter is close to that of the image passage 2. It can accurately determine the position of the catheter and improve the accuracy of the intubation, thus improving the effect of examination and treatment. When the larger-sized catheter passes through the guide groove 3, the elastic mechanism can elastically deform by the elastic force. The catheter may push the elastic mechanism away to ensure the rapid and smooth insertion of the cannula. Because of the flexibility of the elastic mechanism, the guide groove 3 can be adapted to different types of catheters, which not only solves the problem of the displacement of the small-sized catheter before, but also avoids the problem that the hard material hinders the passage of the large-sized catheter.

Figure 2:
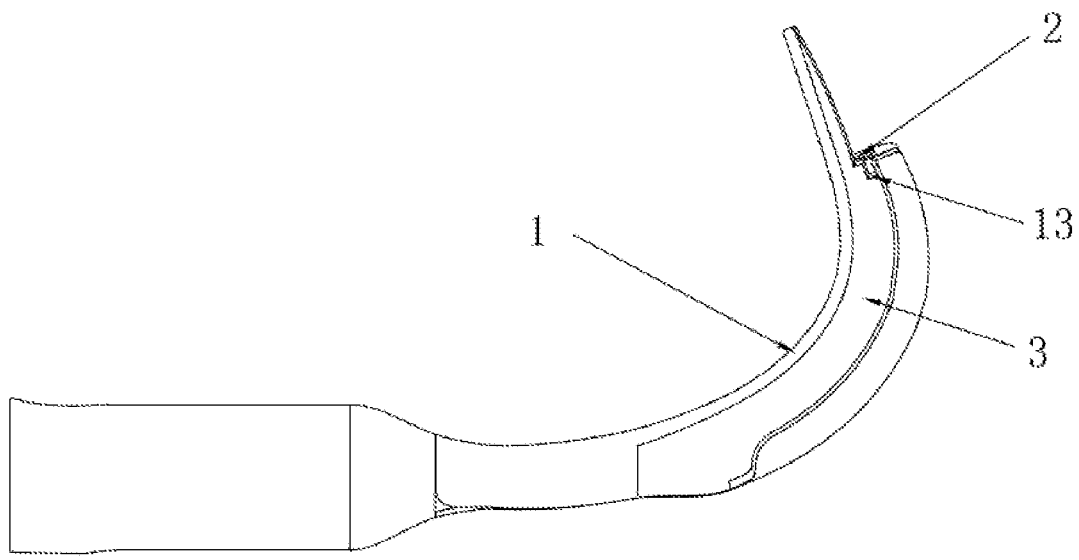
FIG. 2 is a left side view of a second embodiment of the present disclosure.

According to FIG. 1 and FIG. 2, the bottom plate 4 in the first embodiment and the second embodiment is an integrated structure. The elastic mechanism of the first embodiment in FIG. 1 includes a third elastic member 12 disposed at the distal end of the bottom plate 4. The third elastic member 12 is located on the side of the guide plate 5 facing the spatula 1, which lifts the catheter. The third elastic member 12 shown in FIG. 1 is a spring, and the spring is vertically disposed. In actual production, the third elastic member 12 can also be a planar elastic piece, and the planar elastic piece is fixed near one end of the bottom plate 4, and is lifted away from the end of the bottom plate 4. Alternatively, a convex arc-shaped elastic piece may be selected, the arc-shaped elastic piece is fixed at both ends, and the middle is convex toward the spatula 1. The third elastic member 12 has an elastic force in the vertical direction of the bottom plate, and a butterfly-shaped elastic piece or the like with elastic force in the axial direction may also be selected. The elastic mechanism of the second embodiment in FIG. 2 includes a projection block 13 provided on the upper surface of the distal end of the bottom plate 4, and the projection block 13 is made of an elastic material. The projection block 13 in FIG. 2 are elongated and located at the distal end of the guide plate 5. In actual production, the projection block 13 may also have different shapes such as a triangle shape, an arc shape, a polygon, etc., and may be arranged in different shapes such as strips, continuous dots, block shape etc., It may be disposed at different positions such as a middle portion, an end portion of the guide plate 5.

Except that the elastic mechanism is directly disposed on the bottom plate 4 and the bottom plate 4 is directly used for limiting the position, the elastic mechanism of the embodiment of FIGS. 3 to 11 further includes a guide plate 5 connected to the distal end of the bottom plate 4. The distal end of the guide plate 5 is connected to the bottom plate 4, the two sides of the guide plate 5 are not limited, such that the guide plate 5 has elasticity which moves up and down along the connecting side. The left and right sides of the guide plate 5 are connected to the image channel 2, and the front and rear sides of the guide plate 5 are not limited, so that the guide plate 5 has elasticity which moves up and down along the connection of the image channel 2. There is a peak with the smallest distance between the guide plate 5 and the spatula 1 exist on the side of the guide plate 5 facing the spatula 1. The peak makes the catheter lifted. The guide plate 5 connected to the bottom plate 4 is used for limiting in this solution.

Figure 10:
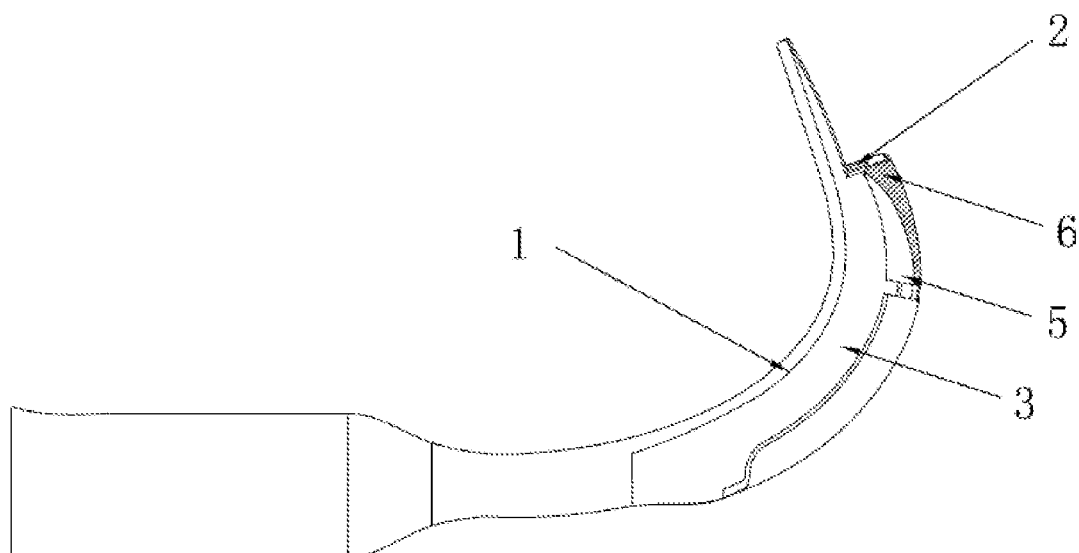
FIG. 10 is a left side elevational view, partly in section, of the tenth embodiment of the present disclosure.
Figure 11:
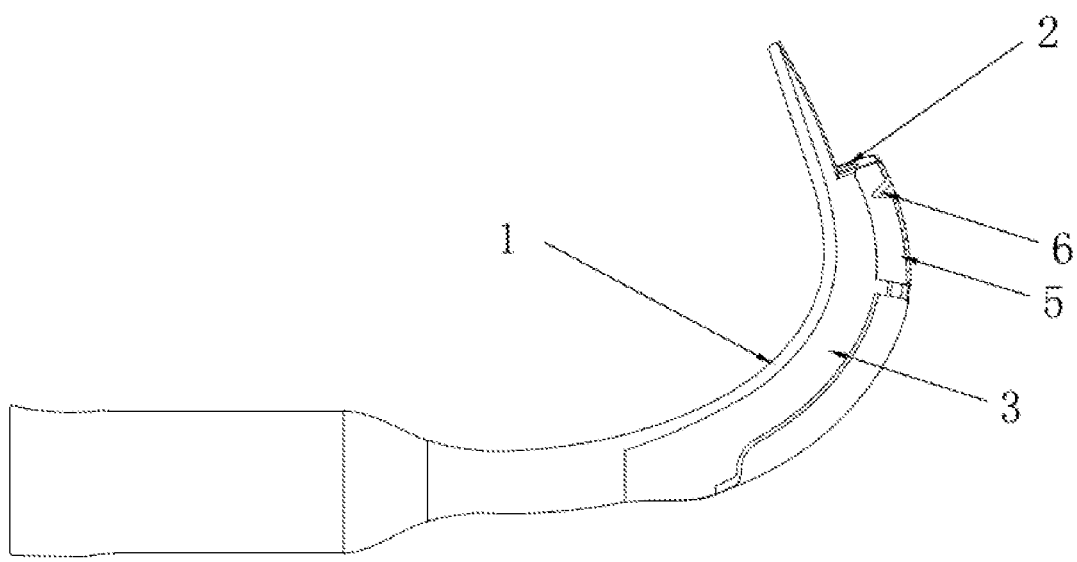
FIG. 11 is a left side elevational view, partly in section, of the eleventh embodiment of the present disclosure.

Referring to the embodiments of FIGS. 3 to 9, the distal end of the guide plate 5 is tilted toward the spatula 1 with the peak the distal end of the guide plate 5. Referring to the embodiments in FIG. 10 and FIG. 11, the guide plate 5 is provided with a protrusion 6, the peak is the apex of the protrusion 6. The protrusions 6 in FIG. 10 and FIG. 11 are two different structures. In the tenth embodiment, the surface of the guide plate 5 is curved and the distal end is lifted. In the eleventh embodiment, the surface of the guide plate 5 is provided with a triangular ridge. In actual production, the protrusion block 13 can also be different shapes, such as rectangular, cylindrical, polygonal, etc. It may be provided in strips, planar, blocks, and the like, and may be disposed at different positions, such as in the middle portion, in the end portion, and the like of the guide plate 5, It is not limited to the embodiments shown in the accompanying drawings.

Figure 3:
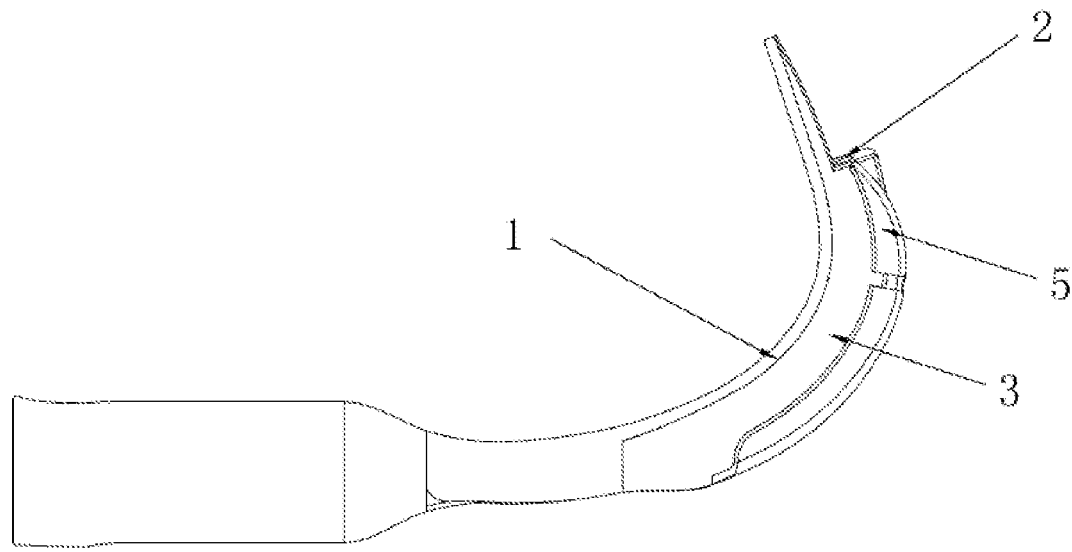
FIG. 3 is a left side view of a third embodiment of the present disclosure.
Figure 4:
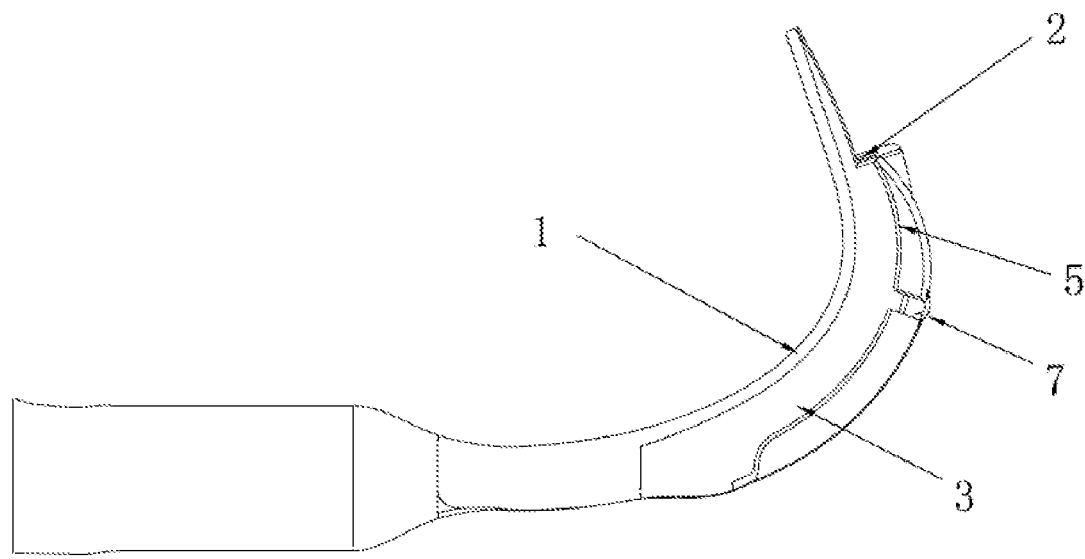
FIG. 4 is a left side view of the fourth embodiment of the present disclosure.

Referring to the third embodiment in FIG. 3, the elastic mechanism is the body of the guide plate 5, the guide plate 5 is made of an elastic material, the guide plate 5 itself has an elastic force, and the guide plate 5 exerts an elastic force against a small catheter by using the tilted distal end or the protrusion provided, while a big catheter pushes the elastic guide plate 5 away. Referring to the fourth embodiment in FIG. 4, the bottom plate 4 and the guide plate 5 are provided at the joint with an elastic arm 7 made of an elastic material. The elastic arm 7 at the joint has elasticity so that the coupled guide plate 5 can rotate around the elastic arm 7. In the working state, the guide plate 5 may rotate and press against the catheter in the direction of the spatula 1, and can also reversely rotate and make way for the catheter toward the spatula 1.

Referring to the embodiments of FIGS. 5 to 8, the guide plate 5 is hinged to the bottom plate 4, and the guide plate 5 is also connected with a reset device which makes the guide plate 5 to have a tendency to rotate toward the spatula 1 around the hinge shaft. The reset device provides a pulling force to rotate the guide plate 5 toward the spatula 1. The pulling force is converted into the pressure applied to the catheter by the guide plate 5, and the catheter is pushed toward the spatula 1.

Figure 5:
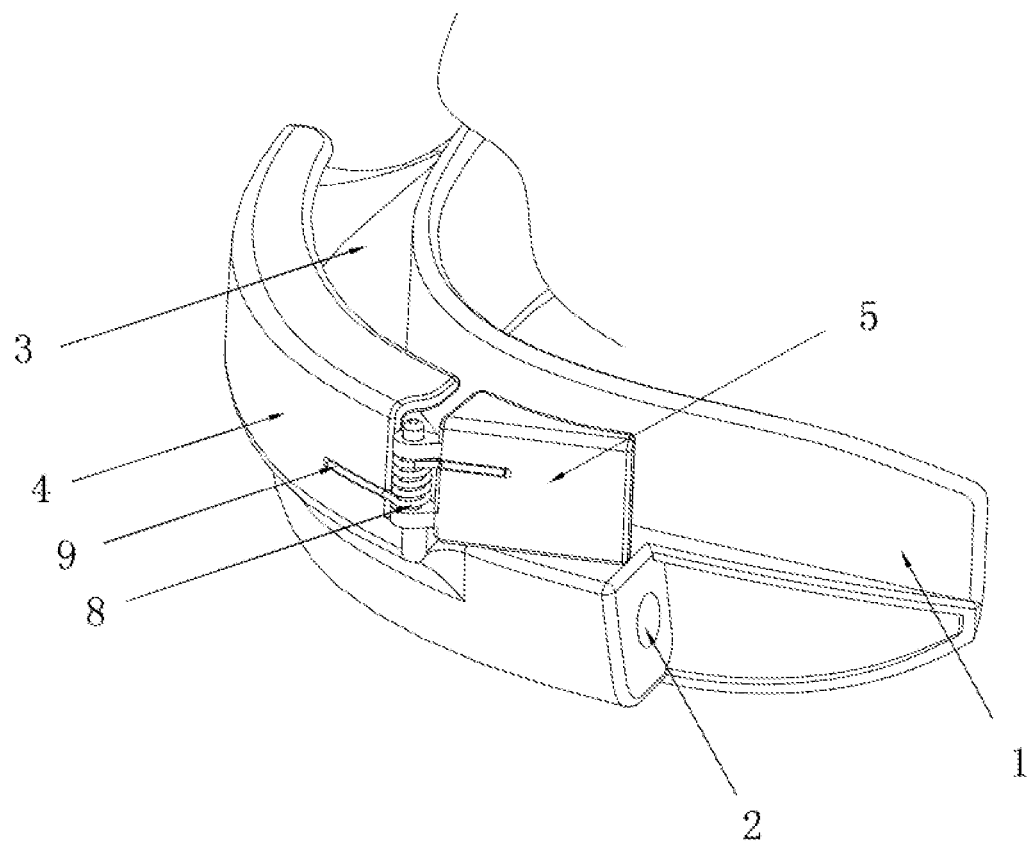
FIG. 5 is a schematic structural view of a fifth embodiment of the present disclosure.

Referring to the fifth embodiment of FIG. 5, the reset device is a first elastic member 8 sleeved on the hinge shaft of the guide plate 5 and the bottom plate 4. The first elastic member 8 has a circumferential torsion elastic force. In the present embodiment, the first elastic member 8 is a torsion spring, and the torsion bars 9 on both sides of the torsion spring are respectively located below the bottom plate 4 and the guide plate 5. The torsion spring applies torque to the guide plate 5, the guide plate 5 converts the torque into the pressure against the catheter. When the large pipe passes, the torsion spring is deformed, and the guide plate 5 can quickly rotate in the reverse direction of the spatula 1.

Figure 6:
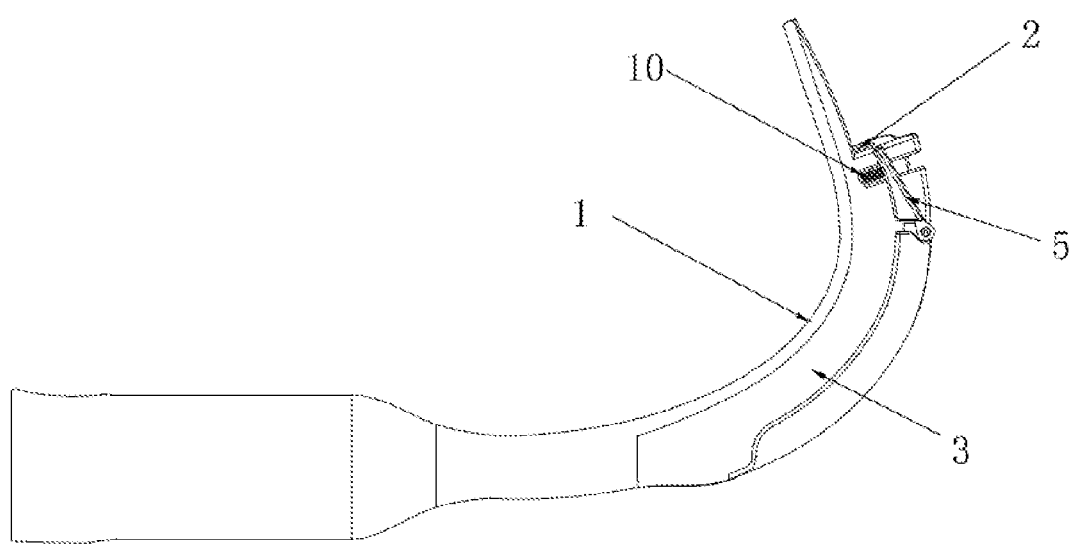
FIG. 6 is a schematic structural view of a sixth embodiment of the present disclosure.
Figure 7:
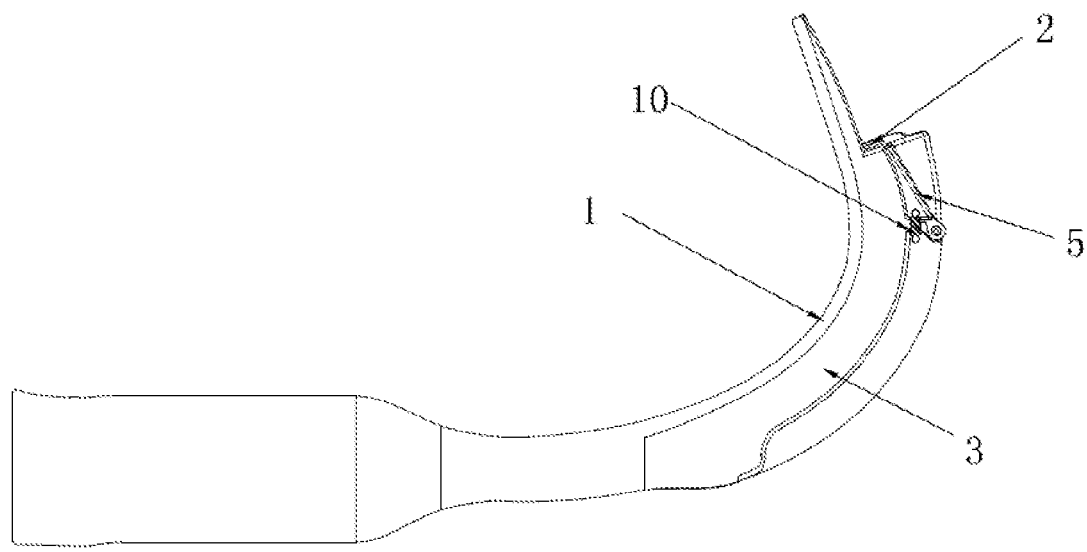
FIG. 7 is a left side view of a seventh embodiment of the present disclosure.

Referring to the embodiments of FIG. 6 and FIG. 7, the reset device is a second elastic member 10 having an axial elastic force, and two ends of the second elastic member 10 are respectively connected to the guide plate 5 and the guide groove 3. The second elastic member 10 in the sixth embodiment is a spring, and the upper end of the spring is connected to the side wall of the guide groove 3, and the lower end of the spring is connected to the guide plate 5. The second elastic member 10 in the seventh embodiment is a tension spring, one end of the tension spring is connected to the side wall of the guide groove 3, and the other end of the tension spring is connected to the guide plate 5. The axially stretched second elastic member 10 is connected at one end to the fixed guide groove 3, and the other end is connected to the guide plate 5, and the guide plate 5 can be pulled into the guide groove 3. The tension of the second elastic member 10 is converted into the pressure applied to the catheter by the guide plate 5. When the guide plate 5 needs to be reversely rotated toward the spatula 1, the second elastic member 10 is stretched. The process is simple and fast. In addition to the tension spring and spring shown in FIGS. 6 and 7, the second elastic member 10 may also be selected from other products such as pressure spring.

Figure 8:
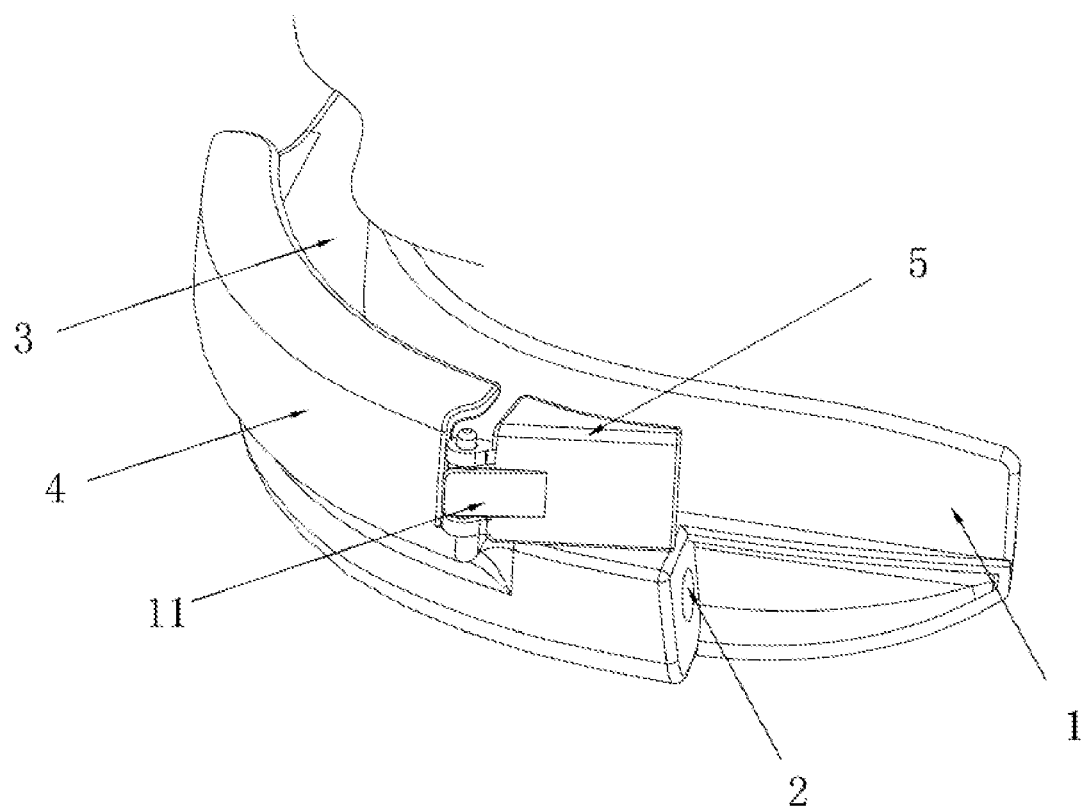
FIG. 8 is a left side view of the eighth embodiment of the present disclosure.

Referring to the eighth embodiment of FIG. 8, the reset device is an elastic plate 11. The lower end of the elastic plate 11 is fixedly connected with the guide groove 3, and the upper end is in contact with the side of the guiding plate 5 facing away from the spatula 1. The elastic plate 11 is made of an elastic material. The lower end of the elastic plate 11 in the eighth embodiment is fixedly connected to the hinge shaft. The elastic plate 11 is a flat plate, and the plate body of the elastic plate 11 is attached to the back of the guide plate 5. The elastic plate 11 applies an elastic force to the guide plate 5, and the elastic force is converted into the pressure applied to the catheter by the guide plate 5. When the guide plate 5 is rotated in the reverse direction of the spatula 1, the elastic plate 11 is deformed so that the guide plate 5 can be smoothly rotated. The elastic plate 11 may also be a curved plate. The lower end of the elastic plate 11 may also be connected to the bottom plate 4.

Figure 9:
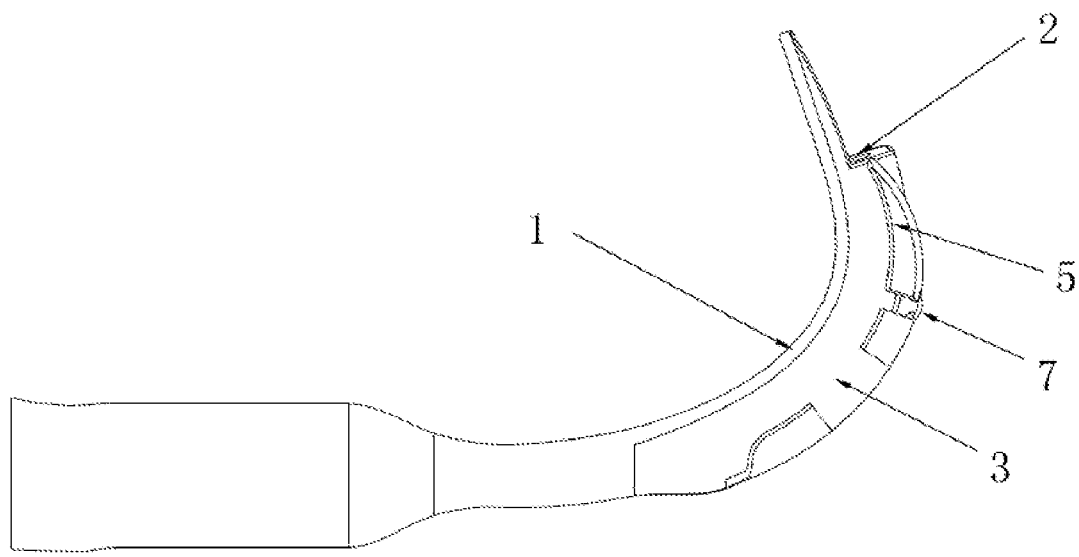
FIG. 9 is a left side view of a ninth embodiment of the present disclosure.

Referring to the ninth embodiment of FIG. 9, the guide groove 3 in this embodiment is of a discontinuous structure. The guide plate 5 is located at the distal end of the last section of the guide groove 3. In actual production, the guide groove 3 may be structured without side walls. The second elastic member 10 is fixed between the bottom plate 4 and the guide plate 5. The selection of elastic mechanism is various and can meet different demands of production and use. The improved laryngoscope blade has various structures, which improves the imaging effect and improves the feeling of use.

With regard to the laryngoscope of the second aspect of the present application, the laryngoscope includes a handle, and any of the above-mentioned laryngoscope blade is inserted at the distal end of the handle, and the laryngoscope using the laryngoscope blade can also be fit to different types of catheters when used, with the insertion of the catheter is more precise and the effect is better.

The preferred embodiments of the present disclosure have been described in details as the above, but the invention is not limited to the embodiments. Those skilled in the art can make various equivalents modifications or alternatives without departing from the spirit of the invention. Such equivalent modifications or alternatives are intended to be included within the scope of the claims.

What is claimed is:

1. A laryngoscope blade comprising:
   a spatula;
   at least one image channel disposed under the spatula;
   and a guide groove besides the image channel for allowing a catheter passing through;
   the guide groove comprising at least one bottom plate extending in a same direction as the spatula, a distal end of the bottom plate being provided with an elastic mechanism pushing the catheter to the spatula;
   wherein said elastic mechanism comprise a guide plate arranged at the distal end of the bottom plate, a peak with a smallest distance between the guide plate and the spatula is provided on said guide plate facing one side of the spatula, for lifting the catheter;
   wherein one side of left and right sides of the guide plate is connected to the image channel, and an other side is tilted toward the spatula.

2. The laryngoscope blade of claim 1, wherein a front end of the guide plate is connected to the bottom plate, and a distal end of the guide plate is tilted toward the spatula.

3. The laryngoscope blade of claim 1, wherein the guide plate is provided with a projection.

4. The laryngoscope blade of claim 1, wherein the guide plate is made of an elastic material.

5. The laryngoscope blade of claim 1, wherein a junction of the bottom plate and the guide plate is provided with an elastic arm made of an elastic material.

6. The laryngoscope blade of claim 1, wherein the guide plate is hinged to the bottom plate, the guide plate is further connected with a reset device, and the reset device makes the guide plate having a tendency to rotate toward the spatula around a hinge shaft.

7. The laryngoscope blade of claim 6, wherein the reset device is a first elastic member sleeved on the hinge shaft of the guide plate and the bottom plate, the first elastic member has an elastic force of circumferential torsion, and torsion bars on both sides of the first elastic member are respectively located below the bottom plate and the guide plate.

8. The laryngoscope blade of claim 6, wherein the reset device is a second elastic member having an axial elastic force, and two ends of the second elastic member are respectively connected to the guide plate and the guide groove.

9. The laryngoscope blade of claim 6, wherein the reset device is an elastic plate, and a lower end of the elastic plate is fixedly connected with the guide groove, and an upper end is in contact with one side of the guide plate facing away from the spatula, the elastic plate is made of an elastic material.

10. A laryngoscope, comprising: a handle coupled to the laryngoscope blade of claim 1.

11. A laryngoscope blade comprising:
    a spatula;
    at least one image channel disposed under the spatula;
    and a guide groove besides the image channel for allowing a catheter passing through;
    the guide groove comprising at least one bottom plate extending in a same direction as the spatula, a distal end of the bottom plate being provided with an elastic mechanism in an extension direction, for pushing the catheter to the spatula;
    wherein said elastic mechanism comprises a third elastic member disposed at the end of the bottom plate, and the third elastic member is located at a side of a guide plate facing the spatula, the third elastic member lifts the catheter;
    or,
    wherein said elastic mechanism comprises a projection block provided on an upper surface of the distal end of the bottom plate, said projection block is made of an elastic material.

* * * * *